United States Patent
Ottuso et al.

(10) Patent No.: US 8,088,093 B2
(45) Date of Patent: Jan. 3, 2012

(54) WOUND PENETRATING HEMOSTATIC DEVICE IMPREGNATED WITH COAGULANT, ANTIBIOTIC AND/OR ANESTHETIC

(76) Inventors: Patrick Ottuso, Vero Beach, FL (US); Vincent R. Snyder, Vero Beach, FL (US)

(*) Notice: Subject to any disclaimer, the term of this patent is extended or adjusted under 35 U.S.C. 154(b) by 367 days.

(21) Appl. No.: 12/501,738

(22) Filed: Jul. 13, 2009

(65) Prior Publication Data
US 2010/0036308 A1  Feb. 11, 2010

Related U.S. Application Data

(60) Provisional application No. 61/087,080, filed on Aug. 7, 2008.

(51) Int. Cl.
*A61F 13/20* (2006.01)
*A61F 13/15* (2006.01)
*A61M 35/00* (2006.01)

(52) U.S. Cl. ............ 604/15; 604/11; 604/12; 604/13; 604/14; 604/362; 604/363; 604/360; 604/309; 604/311

(58) Field of Classification Search ............ 604/11–18, 604/309, 311; 602/48, 69
See application file for complete search history.

(56) References Cited

U.S. PATENT DOCUMENTS

| | | | |
|---|---|---|---|
| 2,120,367 A * | 6/1938 | Lewis | 604/218 |
| 2,290,886 A * | 7/1942 | Lenz | 604/309 |
| 4,895,559 A * | 1/1990 | Shippert | 604/15 |
| 4,900,303 A * | 2/1990 | Lemelson | 604/514 |
| 5,112,325 A * | 5/1992 | Zachry | 604/362 |
| 5,263,927 A * | 11/1993 | Shlain | 604/13 |
| 5,295,952 A * | 3/1994 | Pietrafitta | 604/1 |
| 5,312,435 A * | 5/1994 | Nash et al. | 606/213 |
| 5,326,350 A * | 7/1994 | Li | 623/23.72 |
| 5,395,309 A * | 3/1995 | Tanaka et al. | 604/18 |
| 5,478,308 A * | 12/1995 | Cartmell et al. | 602/57 |
| 5,514,158 A * | 5/1996 | Kanesaka | 606/213 |
| 5,545,178 A * | 8/1996 | Kensey et al. | 606/213 |
| 5,836,970 A * | 11/1998 | Pandit | 606/213 |
| 6,008,189 A * | 12/1999 | Inamoto et al. | 514/20.9 |
| 6,183,436 B1 * | 2/2001 | Korteweg et al. | 604/96.01 |
| 6,475,177 B1 * | 11/2002 | Suzuki | 604/11 |
| 6,517,509 B1 * | 2/2003 | Shippert | 604/11 |
| 6,730,057 B2 * | 5/2004 | Zhao et al. | 604/11 |
| 6,808,485 B2 * | 10/2004 | Zunker | 600/29 |
| 2002/0026140 A1 * | 2/2002 | McNamara | 604/12 |
| 2002/0193726 A1 * | 12/2002 | Cimber | 604/11 |
| 2004/0172000 A1 * | 9/2004 | Roe et al. | 604/361 |
| 2005/0133387 A1 * | 6/2005 | Cohen et al. | 206/233 |

(Continued)

*Primary Examiner* — Leslie Deak
*Assistant Examiner* — Susan Su
(74) *Attorney, Agent, or Firm* — Berenato & White, LLC

(57) ABSTRACT

A tampon assembly used for penetration injuries to provide hemostasis and simultaneous broad spectrum antibiotic/anesthetic application. The tampon includes a helically-wound absorbent member impregnated with coagulant, covered with biodegradable or plastic accordion-pleated sheath including a bioluminescent tape outer marker. The device would also contain a measured dose of antibiotic/anesthetic suspension sealed within the confines of the outer sheath. The outer sheath would preferably have a perforated petal-shaped tip to enable wound insertion followed by through passage of the contained wound packing and treatment liquids/emulsions, etc. A radio opaque cotton withdrawal string would attach to the absorbent member at the end facing the wound opening. An insertion stick/plunger is used for tampon deposition within the wound. Manual pressure on the plunger would cause seal rupture and expulsion of the wound packing and treatment through the ruptured tip of the sheath. The tampon device may be of various sizes or shapes to conform to various injuries. It may be used intra-operatively during surgery as well.

9 Claims, 2 Drawing Sheets

U.S. PATENT DOCUMENTS

2006/0004318 A1* 1/2006 Przepasniak et al. ............ 604/14
2006/0247571 A1* 11/2006 Hayes et al. .................... 604/14
2008/0015481 A1* 1/2008 Bergin et al. ................... 602/46

* cited by examiner

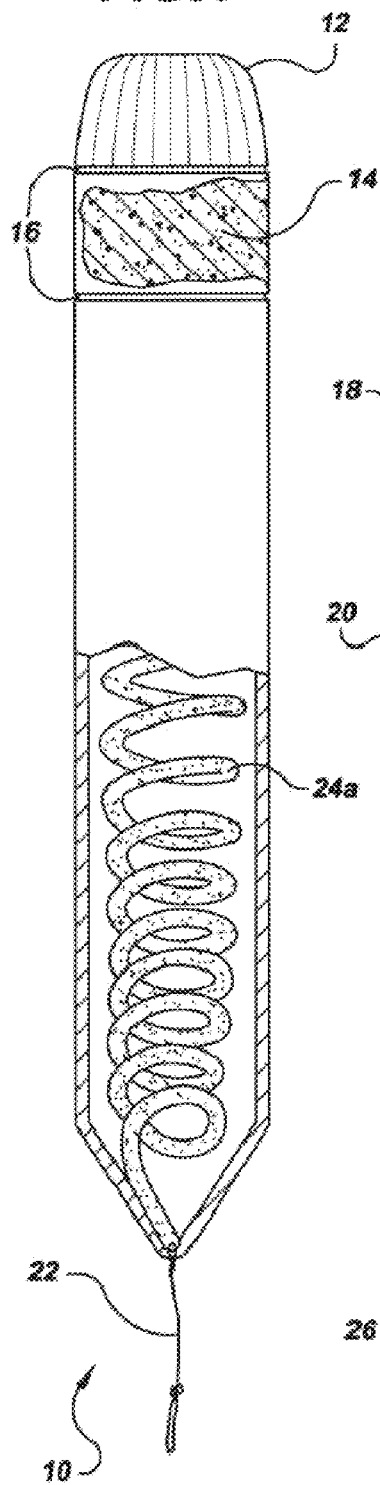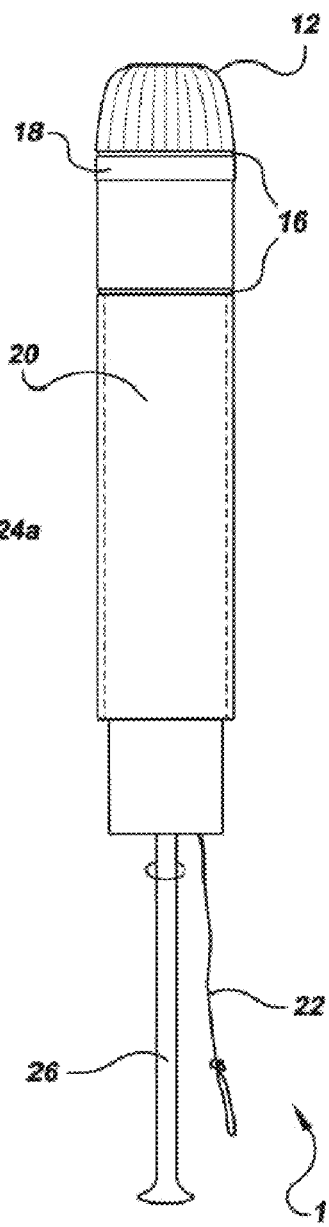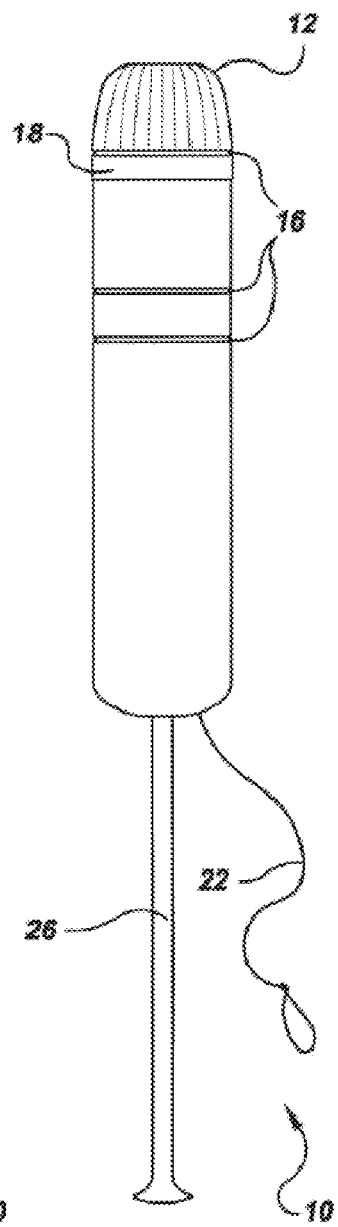

WOUND PENETRATING HEMOSTATIC DEVICE IMPREGNATED WITH COAGULANT, ANTIBIOTIC AND/OR ANESTHETIC

CROSS REFERENCE TO RELATED APPLICATIONS

This application is based on and claims the benefit of the filing date of U.S. provisional application Ser. No. 61/087,080, filed Aug. 7, 2008, and incorporated herein by reference in its entirety.

FIELD OF THE INVENTION

The present invention relates to a hemostatic device presented as a tampon for penetrating and/or perforating injuries due to projectiles and/or devices that may cause perforating injuries to the body.

BACKGROUND OF THE INVENTION

Wound dressings have a history as long as the story of mankind. Each generation and culture has developed their own advances in wound care, typically driven by the type of wound encountered. Various coverings/bandages have been the subject of many a medical advance and include wrappings, combination wrapping and gauze, treated dressings (topical antibiotics, anesthetics, coagulants, etc.) have all been developed and are available in many forms. (BAND-AID®, NEOSPORIN®, Aerosols, etc.)

The general concept of a tampon wound dressing to be inserted into a cavity using a sheath where the tampon may be coated with antibiotics or lubricant and where the tampon is provided with a removal string is known, see U.S. Pat. No. 6,183,436. Likewise, U.S. Pat. App. 2008/0015481 A1 discloses having a wound dressing inserted into a puncture wound. Further, U.S. Pat. No. 5,836,970 discloses the use of chitosan in a wound dressing, and U.S. Pat. No. 5,478,308 discloses the use of spiral packing for the wound packing material.

The foregoing advances notwithstanding, rapid effective treatment for puncture wounds is still far from perfected. These wounds are encountered in a variety of settings. In a combat, E.R., or other EMT type setting where fast effective action is critical, past solutions fall short. Either the correct combination of features is not available, in the right size, or the applied treatment is unrecognized during later steps (owing to blood soaking, etc.) and further effective treatments are slowed, misled, or otherwise hampered.

SUMMARY OF THE INVENTION

The present invention is directed toward providing a hemostatic device presented as a tampon. The tampon may be impregnated with a coagulant, a broad spectrum antibiotic, and/or an anesthetic. The tampon device is made up of the following elements:

A wound insertable outer sheath surrounding an absorbent material made of cotton fiber and/or rayon coagulant material (containing one or more of: chitosan, dry fibrin sealant, volcanic rock, ionic silver, and/or recombinant factor seven) and an extraction radio opaque cotton string firmly connected to an end thereof. In addition, the tampon system may include (in liquid or suspension or emulsion) a broad spectrum antibiotic contained by a cellophane or biodegradable seal, and an applicator stick or plunger to place the tampon and release the sealed mixtures noted previously. The sheath may include an optional petroleum jelly or other lubricating substance on the sheath or may be coated with a low friction bio compatible layer. The system may further include lidocaine 1% with epinephrine 1:100,000 and, a 5 mm wide bioluminescent marker tape so that the tampon system may be visible in low light treatment circumstances.

The present invention may be defined in part by reference to its objects. In a preferred embodiment, it is an object of this invention to provide a helically-wound absorbent material embedded with a coagulant substance within an accordion pleated petal tipped or perforated tipped outer covering or sheath. In addition, enclosed within the body of the tampon is a measured dose of a broad-spectrum antibiotic and/or anesthetic in suspension or liquid.

It is another object of the present invention to provide a hemostatic device as a tampon with an accordion pleated sheath, which provides ready insertion into a wound by a rearwardly oriented plunger or similar applicator. The absorbency may be provided by a helically wound member absorbent material.

It is another object of the present invention to provide a coagulant effect by chitosan, dry fibrin sealant, volcanic rock, ionic silver, and/or recombinant factor seven or combinations thereof.

It is another object of the present invention to provide a conventional radio opaque cotton string used to withdraw the tampon from the wound once the desired coagulant effect and/or absorbency is achieved upon transport of the wound victim to a controlled surgical setting. The radio opaque string can be located through the use of radiography if it is otherwise lost in the wound.

It is another object of the invention to provide a highly visible, rapid, effective puncture wound treatment wherein a bio luminescent marker enables accurate use of the wound treatment system in low light situations.

It is another object of the present invention to provide for the use of the tampon during intra-operative procedures where a hemostatic effect and/or local antibiotic and/or anesthetic effect into a surgical site is desired.

These and other objects of the invention will be described in the following descriptive paragraphs. The invention is not limited by this description, but rather by the understanding and inferences drawn by one of ordinary skill in this field.

BRIEF DESCRIPTION OF THE DRAWINGS

FIG. 1 represents a cross sectional view of a hemostatic device embodying the present invention showing a pleaded or petal end, compartmentalized antibiotic and/or anesthetic suspension with associated seals and a helically coiled coagulant embedded absorbent material with an end attached radio opaque cotton string;

FIG. 2 represents a side view of the hemostatic device assembly and associated plunger ready for insertion into a penetrating wound;

FIG. 3 represents the hemostatic device depicting a pleated or petal end;

DETAILED DESCRIPTION

Figure 4:
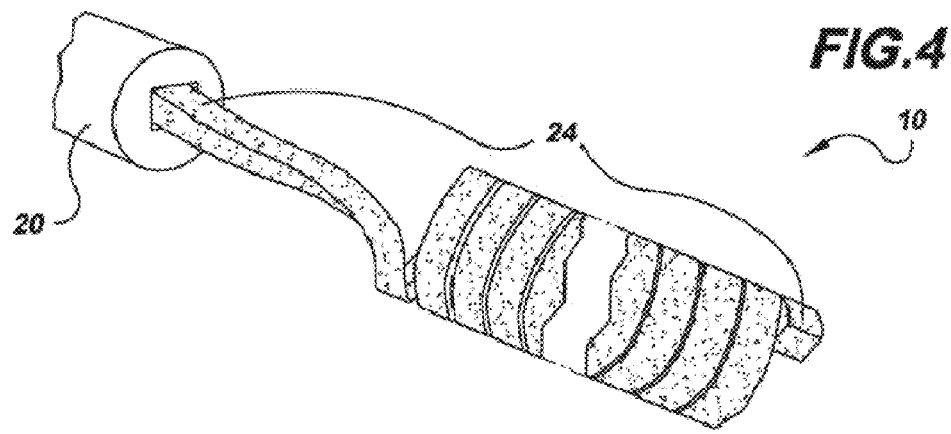
FIG. 4 represents a diagrammatic and isometric view of a partially extruded portion of the helically coiled absorbent material of FIG. 1.

With reference to FIGS. 1 and 2: Illustrated is a preferred embodiment of the present invention consisting of a cylindrical sheath 20 that covers and protects the coagulant embedded absorbent material 24a preferably made of cotton or rayon. The absorbent material 24a is treated with any of chitosan, dry fibrin sealant, volcanic rock, ionic silver, and/or recombinant factor seven in various combinations. The absorbent material treatment may involve processes including but not limited to soaking, pressing, pressure spraying, freeze drying, or heating.

Within the sheath, and physically separated by a rupturable seal 16 from the absorbent material 24a, is a standard dose 14 of a liquid, suspension, or emulsion comprising a broad spectrum antibiotic which may be mixed with an anesthetic. The seal 16 above the absorbent material may compartmentalize the anesthetic. The absorbent material 24a may be pressed and sealed to a radio opaque cotton fiber string 22 which functions as a removal device to extrude the tampon from the wound post treatment. As shown, a bioluminescent tape 18 is attached circumferentially to the shaft/sheath of the tampon to aid in visualizing the device during low light usage.

In embodiments of the present invention, the sheath 20 may be composed of bio compatible plastic, composite, stainless steel, or a biodegradable (even, potentially, bio dissolving or absorbing) material. The sheath may be pleated or smooth, and may optionally include a lubricating coating. The sheath tip 12 may be perforated, solid (but frangible), or divided.

In other preferred embodiments, the sheath size and shape may be varied, (e.g. color coded sizing in 2-3 ml caliber increments) along with the size (caliber and length), shape and chemical make-up of the absorbent material. The absorbent material may be multi-layered. Single or multiple combinations of the antibiotic and anesthetic agents may be used. The anesthetic may or may not include epinephrine and/or sodium bicarbonate.

Figure 5:
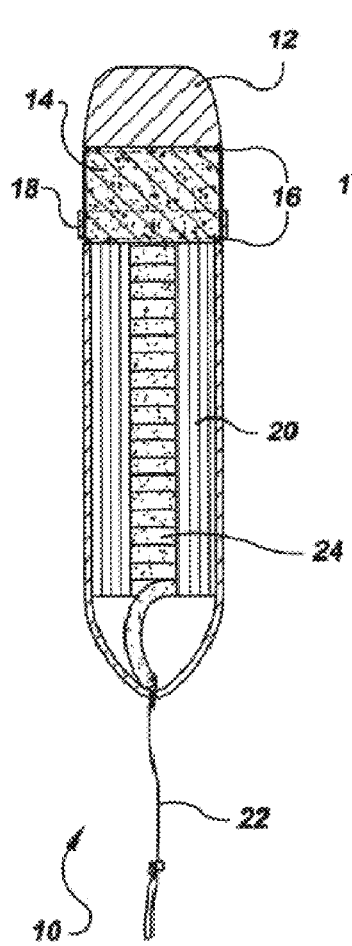
FIG. 5 represents a sectional view of the hemostatic device with the sheath whereby its end is pleated or petal shaped, the antibiotic and/or anesthetic suspension is compartmentalized towards the tip of the hemostatic device in a cellulose membrane sealed chamber, and the helically coiled coagulant embedded material is within the pleated sheath and the radio opaque cotton string for removal is attached.

In another preferred embodiment, the tampon may be made by providing a primary sheet of absorbent material to form the corpus or body of the device. Multiple sheets may be added to increase absorbency. In one form of the invention, the coagulant is deposited between multiple corpus sheets. In another form of the invention, the coagulant is embedded into one or more sheets. The superimposed sheets are then rolled and formed into the desired shape of the tampon. The absorbent sheets 24 may also be coiled into a helical arrangement within the sheath as shown in FIGS. 4 and 5. A coating of petroleum jelly or other lubricating substance may be used on the exterior of the sheath as an assist for insertion of the tampon into the wound. The bioluminescent tape 18 also shown is used for visualization of the device, as previously noted, during poor lighting or nighttime use.

In another preferred embodiment, the antibiotic dosing may include but is not limited to the use of broad-spectrum antibiotics. One potential antibiotic would be imipenam in combination with cilastatin in a first time dose of 500milligrams.

Figure 6:
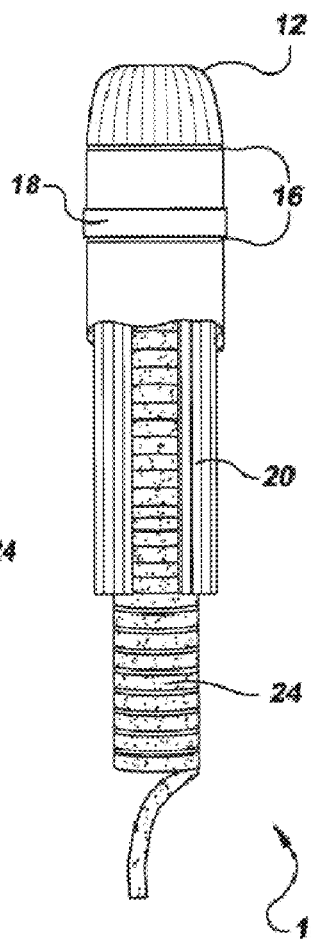
FIG. 6 represents a partially sectioned isometric view of the hemostatic device showing the absorbent material being wound or otherwise conformed into a tight, contiguous, hollow body so as to provide a substantially smooth and contiguous outer surface area.
Figure 7:
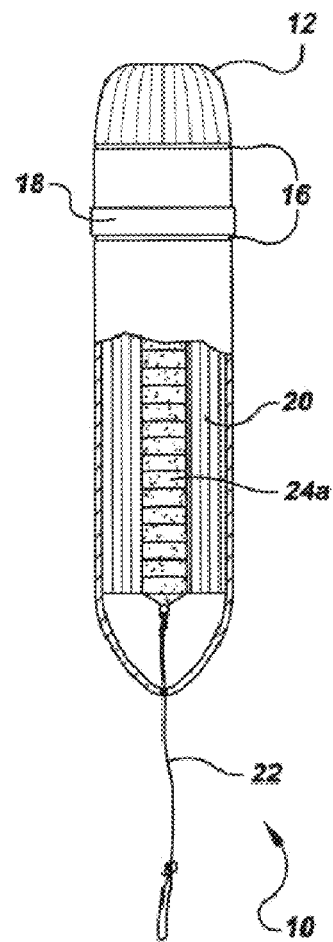
FIG. 7 represents a lateral view of the pleated end of the sheath with antibiotic suspension and coagulant embedded absorbent material attached to a radio opaque withdrawal string.

In another preferred embodiment, referring to FIGS. 2 and 3, the sheath 20 and plunger 26 are preferably plastic or biodegradable material. The sheath tip 12 is perforated. The plunger 26 is used to insert the sheath 20 into the wound. The plunger 20 is also used to disperse the absorbent material with any included coagulant, antibiotic or anesthetic suspension, liquid or emulsion 24 and 24a shown in FIGS. 5, 6, and 7 into the wound by pressure placed on the plunger.

Pressure on the plunger allows for rupture of the seal 12, pushing the active materials from the tampon into the wound. The sheath 20, preferably accordion pleated and lubricant coated, can then be removed. Once in a hospital or surgery setting, the absorbent material can be removed using the radio opaque cotton string 22 attached to the hemostatic "plug".

In another preferred embodiment, a modification of the tampon comprising biodegradable cellulose absorbent material 24a may be used during controlled surgical procedures to aid in stemming intra-operative bleeding. The hemostatic device may be used in providing a concentrated dose of antibiotic 14 at the injury site, including use in gastrointestinal, hepatic, head and neck, urologic, gynecologic surgery.

In another preferred embodiment, the tampon may be used to stem bleeding from a perforating injury such as a projectile or knife wound. The tampon may be used to deliver a broadspectrum antibiotic 14 into such a wound. Following insertion into a wound, when necessary, the radio opaque withdrawal string 22 is engaged in and by a withdrawal action and motion, the tampon assembly is moved toward the injury opening. The tampon may be impregnated with a coagulant within the fibers of the cotton or other absorbent material 24a. A broad-spectrum antibiotic 14 may be enclosed within the tampon delivery system. The tampon is inserted into the wound and kept in place until the patient is transported to a medical facility where the tampon can be removed.

While the present invention has been described in terms of specific embodiments, it is to be understood that the invention is not limited to these disclosed embodiments. The present invention may be embodied in many different forms and should not be construed as limited to the embodiments set forth herein: rather, these embodiments are provided by way of illustration only and so that this disclosure will be thorough, complete, and fully convey the full scope of the invention to those skilled in the art. It is expected that many modifications and other embodiments of the invention will come to mind to those skilled in the art of which this invention pertains, and which are intended to and are covered by both this disclosure, the drawings, and the claims.

What is claimed is:

1. A hemostatic device for placing wound packing into a puncture type wound, comprising:
   an outer sheath having a forward tipped end adapted for wound insertion and a rearward end;
   an absorbent material coated with a coagulant contained within said sheath and having a radio opaque cotton string attached to an end thereof proximate said rearward end of said sheath;
   a broad spectrum antibiotic also located within said sheath forward of said absorbent material and contained between rupturable seals within said sheath;
   a plunger engaging a rearward end of said absorbent material adjacent said radio opaque string for thrusting said absorbent material forwardly through said sheath and beyond said tipped end into a treated wound; and, said sheath further including a bioluminescent marker on an outer surface thereof to enable usage of said device in low ambient light conditions.

2. The device of claim 1, further comprising:

an anesthetic contained within said sheath.

3. The device of claim 1, wherein:

said absorbent material is rayon and cotton and is treated with one or more materials selected from the group consisting of chitosan, dry fibrin sealant, volcanic rock, ionic silver, and recombinant factor seven.

4. The device of claim 1 wherein said absorbent material comprises a layer configured in a helical coil within said sheath.

5. The device of claim 1 wherein the sheath is covered in a lubricant material for ease of wound insertion.

6. The device of claim 1 wherein said tipped end is accordion pleated.

7. The device of claim 1, wherein said coagulant material is embedded in said absorbent material.

8. The device of claim 1 wherein an anesthetic is used and is mixed with said antibiotic contained between said seals.

9. The device of claim 1 wherein said device is constructed in a plurality of shapes and sizes to accommodate correspondingly sized penetrating injuries.

\* \* \* \* \*

UNITED STATES PATENT AND TRADEMARK OFFICE
CERTIFICATE OF CORRECTION

PATENT NO. : 8,088,093 B2
APPLICATION NO. : 12/501738
DATED : January 3, 2012
INVENTOR(S) : Patrick Ottuso It is certified that error appears in the above-identified patent and that said Letters Patent is hereby corrected as shown below:

Title page, item [76], the second inventor should be listed as
Vincent R. SNEIDER Signed and Sealed this
Twentieth Day of March, 2012

David J. Kappos
*Director of the United States Patent and Trademark Office*